United States Patent
Saito

(10) Patent No.: US 10,591,452 B2
(45) Date of Patent: Mar. 17, 2020

(54) GAS CHROMATOGRAPH

(71) Applicant: Shimadzu Corporation, Kyoto-shi, Kyoto (JP)

(72) Inventor: Maki Saito, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 182 days.

(21) Appl. No.: 15/541,935

(22) PCT Filed: Jan. 26, 2015

(86) PCT No.: PCT/JP2015/051990
§ 371 (c)(1),
(2) Date: Jul. 6, 2017

(87) PCT Pub. No.: WO2016/120963
PCT Pub. Date: Aug. 4, 2016

(65) Prior Publication Data
US 2017/0356890 A1 Dec. 14, 2017

(51) Int. Cl.
G01N 30/00 (2006.01)
G01N 30/86 (2006.01)
G01N 30/32 (2006.01)
G01N 30/54 (2006.01)
G01N 30/02 (2006.01)
(Continued)

(52) U.S. Cl.
CPC ............ *G01N 30/86* (2013.01); *G01N 30/02* (2013.01); *G01N 30/12* (2013.01); *G01N 30/32* (2013.01); *G01N 30/54* (2013.01); *G01N 30/66* (2013.01); *G01N 30/68* (2013.01);
(Continued)

(58) Field of Classification Search
None
See application file for complete search history.

(56) References Cited

U.S. PATENT DOCUMENTS

| 5,508,204 A * | 4/1996 | Norman | G01N 30/30 |
| | | | 210/198.2 |
| 6,148,657 A * | 11/2000 | Satoh | G01N 30/88 |
| | | | 422/84 |
| 2011/0100093 A1* | 5/2011 | Kawana | G01N 30/28 |
| | | | 73/23.42 |

FOREIGN PATENT DOCUMENTS

| JP | 55-46217 U | 3/1980 |
| JP | 04-138359 A | 5/1992 |

(Continued)

OTHER PUBLICATIONS

Article titled "Standby" by Techterms published on Oct. 24, 2007 and available at https://techterms.com/definition/standby.*

(Continued)

*Primary Examiner* — Blake A Tankersley
(74) *Attorney, Agent, or Firm* — Sughrue Mion, PLLC

(57) ABSTRACT

A gas chromatograph is provided which is capable of effectively reducing the amount consumed of a carrier gas, reducing the time and effort required for an operator to manually set parameters, and preventing damages to a column and a detector due to a setting mistake. In a case where a stop operation for the power supply of the gas chromatograph is performed (Yes in step S101), the flow rate of a carrier gas to be supplied to a sample vaporization chamber is decreased and the temperatures of the column and the detector are sufficiently lowered (steps S102 to S104), and then the power supply of the gas chromatograph is switched over from an ON state to an OFF state (step S106).

7 Claims, 10 Drawing Sheets

(51) Int. Cl.
    *G01N 30/12*     (2006.01)
    *G01N 30/66*     (2006.01)
    *G01N 30/68*     (2006.01)

(52) U.S. Cl.
    CPC . *G01N 2030/025* (2013.01); *G01N 2030/126* (2013.01); *G01N 2030/324* (2013.01)

(56) References Cited

FOREIGN PATENT DOCUMENTS

| | | |
|---|---|---|
| JP | 2000-304751 A | 11/2000 |
| JP | 3204106 B2 | 9/2001 |

OTHER PUBLICATIONS

Youtube video titled "windows xp shutdown" by Marie McKinley published on Sep. 3, 2011 and available at https://www.youtube.com/watch?v=nUx-8a9km2Q.*

International Search Report for PCT/JP2015/051990 dated Apr. 21, 2015 [PCT/ISA/210].

Written Opinion for PCT/JP2015/051990 dated Apr. 21, 2015 [PCT/ISA/237].

* cited by examiner

GAS CHROMATOGRAPH

CROSS REFERENCE TO RELATED APPLICATIONS

This application is a National Stage of International Application No. PCT/JP2015/051990 filed Jan. 26, 2015, the contents of all of which are incorporated herein by reference in their entirety.

TECHNICAL FIELD

The present invention relates to a gas chromatograph which introduces a sample vaporized in a sample vaporization chamber into a column together with a carrier gas, and which detects a sample component separated while the sample passes through the column by means of a detector.

BACKGROUND ART

When an analysis is performed by using a gas chromatograph, a carrier gas is supplied to a sample vaporization chamber, and a sample vaporized in the sample vaporization chamber is introduced into a column together with the carrier gas. The column is heated to a high temperature, and a sample component separated while the sample passes through the column is detected in a detector. In order to prevent a damage to the column, a carrier gas is continuously supplied into the column even after the analysis is finished; however, upon exchange of the column or the like, the temperature of the column is sufficiently lowered, and then supply of a carrier gas is stopped (see Patent Document 1 listed below).

An analysis will not be performed for a long time after the power supply of the gas chromatograph has been switched over from an ON state to an OFF state. Therefore, if a carrier gas is continuously supplied after switchover of the power supply, the carrier gas is wastefully consumed. Therefore, an operator conventionally performs work of manually setting parameters in order to lower the temperature of the column and to reduce the flow rate of the carrier gas.

PRIOR ART DOCUMENT

Patent Document

Patent Document 1: Japanese Patent No. 3204106

SUMMARY OF THE INVENTION

Problems to be Solved by the Invention

However, in a configuration where an operator manually sets parameters, there is a possibility that a setting mistake made by the operator will occur. In a case where such a setting mistake occurs, there is a possibility that the column will be damaged. In addition, there is also a possibility that another member such as a detector will be damaged. In particular, in a certain detector such as a thermal conductivity detector (TCD), since a filament provided inside is exposed to a high temperature for a long time, the service life of the filament may be shortened or the filament may be broken in some cases.

As described, when the power supply of the gas chromatograph is switched over from the ON state to the OFF state, it is necessary to pay attention not to damage the detector as well as the column, and the operator needs to carefully set parameters. Since work of setting the flow rate of the carrier gas, which is also required to be performed by the operator, is complicated, a setting mistake is likely to occur and there is a possibility that the flow rate of the carrier gas may not be preferably reduced.

The present invention is made in view of the above circumstances. An object to the present invention is to provide a gas chromatograph capable of effectively reducing the amount consumed of a carrier gas, reducing the time and effort required for an operator to manually set parameters, and preventing damages to a column and a detector due to a setting mistake.

Means for Solving the Problems

A gas chromatograph according to the present invention is a gas chromatograph which introduces a sample vaporized in a sample vaporization chamber into a column together with a carrier gas, and which detects a sample component separated while the sample passes through the column by means of a detector. The gas chromatograph includes a first temperature sensor, a second temperature sensor, a flow rate control unit, an operation reception unit, and a power supply control unit. The first temperature sensor detects the temperature of the column. The second temperature sensor detects the temperature of the detector. The flow rate control unit controls the flow rate of a carrier gas to be supplied to the sample vaporization chamber. The operation reception unit receives an instruction operation for the gas chromatograph. The power supply control unit switches over the power supply of the gas chromatograph. The flow rate control unit decreases the flow rate of the carrier gas to be supplied to the sample vaporization chamber in a case where a stop operation for the power supply of the gas chromatograph is received by the operation reception unit. The power supply control unit switches over the power supply of the gas chromatograph from an ON state to an OFF state in a case where the temperature of the column detected by the first temperature sensor is not higher than a first reference temperature and the temperature of the detector detected by the second temperature sensor is not higher than a second reference temperature in a state where the flow rate of the carrier gas to be supplied to the sample vaporization chamber is not greater than a reference flow rate.

According to such a configuration, in a case where a stop operation for the power supply of the gas chromatograph is performed, the power supply of the gas chromatograph can be switched over from the ON state to the OFF state after the flow rate of the carrier gas to be supplied to the sample vaporization chamber has been decreased and the temperatures of the column and the detector have been sufficiently lowered. As described, by reducing the flow rate of the carrier gas at a time point when a stop operation for the power supply of the gas chromatograph is performed, the amount consumed of the carrier gas can be effectively reduced.

Even in a case where the flow rate of the carrier gas is decreased, since the carrier gas constantly flows into the column and the detector even though the amount of the carrier gas may be small, the column and the detector can be constantly filled with the carrier gas, and the column and the detector can be prevented from being damaged due to high temperature. In addition, since the power supply of the gas chromatograph is switched over from the ON state to the OFF state after the temperatures of the column and the detector have been sufficiently lowered, damages to the column and the detector are prevented even after the power supply is switched over to the OFF state. By automatically performing such control, the time and effort required for an operator to manually set parameters can be reduced and damages to the column and the detector due to a setting mistake can be prevented.

The gas chromatograph may further include a third temperature sensor which detects the temperature of the sample vaporization chamber. In this case, the power supply control unit may switch over the power supply of the gas chromatograph from the ON state to the OFF state in a case where the temperature of the column detected by the first temperature sensor is not higher than the first reference temperature, the temperature of the detector detected by the second temperature sensor is not higher than the second reference temperature, and the temperature of the sample vaporization chamber detected by the third temperature sensor is not higher than a third reference temperature in a state where the flow rate of the carrier gas to be supplied to the sample vaporization chamber is not greater than the reference flow rate.

According to such a configuration, in a case where a stop operation for the power supply of the gas chromatograph is performed, the power supply of the gas chromatograph can be switched over from the ON state to the OFF state after the temperature of the sample vaporization chamber as well as the temperatures of the column and the detector has been sufficiently lowered. Thus, the power supply of the gas chromatograph can be more safely switched over from the ON state to the OFF state.

In a case where a stop operation for the power supply of the gas chromatograph is received by the operation reception unit, the flow rate control unit may set a target flow rate of the carrier gas to be supplied to the sample vaporization chamber to a fixed flow rate which is not greater than the reference flow rate.

According to such a configuration, since the flow rate of the carrier gas is suddenly decreased to be not greater than the reference flow rate in a case where a stop operation for the power supply of the gas chromatograph is performed, the amount consumed of the carrier gas can be effectively reduced.

The flow rate control unit may decrease in stages the target flow rate of the carrier gas to be supplied to the sample vaporization chamber to a flow rate not greater than the reference flow rate according to the temperature of the column detected by the first temperature sensor in a case where a stop operation for the power supply of the gas chromatograph is received by the operation reception unit.

According to such a configuration, in a case where a stop operation for the power supply of the gas chromatograph is performed, since the flow rate of the carrier gas is decreased in stages to be not greater than the reference flow rate, the flow rate of the carrier gas can be gradually decreased while the temperatures of the column and the detector are lowered. At that time, since the flow rate of the carrier gas is gradually reduced according to the temperature of the column, the amount consumed of the carrier gas can be effectively reduced while a damage to the column is prevented.

The gas chromatograph may further include a temperature control unit which automatically lowers a target temperature of the column in a case where a fixed time period has passed in a state where no instruction operation for the gas chromatograph is received by the operation reception unit when the power supply of the gas chromatograph is in the ON state. The target temperature which is automatically set is a temperature lower than the temperature of column upon analysis, and is a temperature (for example, room temperature) which does not cause a damage to the column such as bleed even if the column is maintained at the temperature for a long time.

According to such a configuration, in a case where an operator does not perform an instruction operation for the gas chromatograph for a long time, the temperature of the column is automatically lowered. Therefore, a damage to the column can be effectively prevented.

MODE FOR CARRYING OUT THE INVENTION

Figure 1:
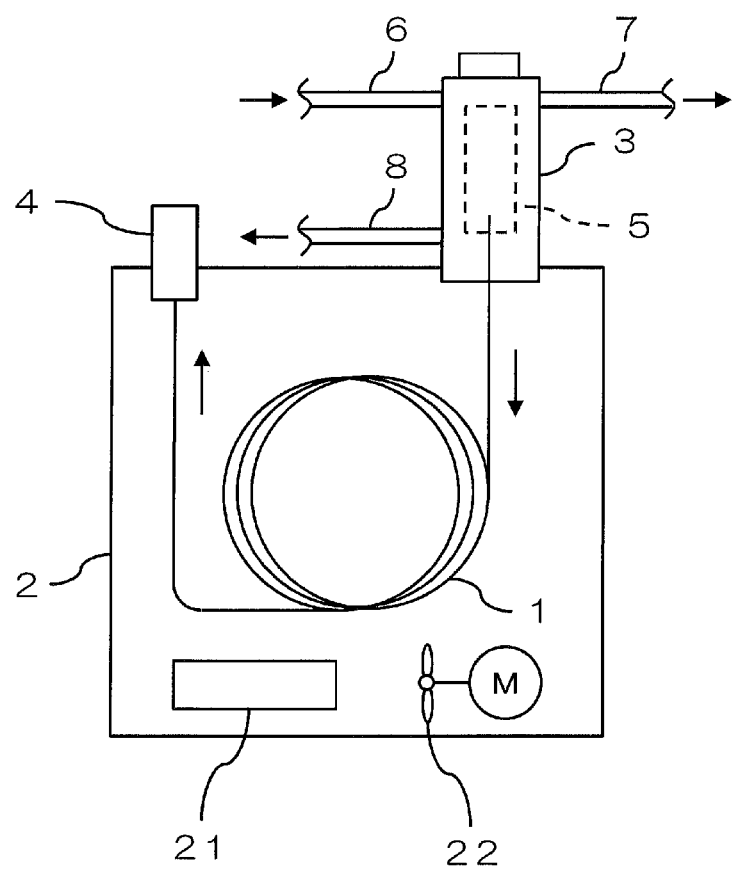
FIG. 1 is a schematic view illustrating a configuration example of a gas chromatograph according to an embodiment of the present invention.

FIG. 1 is a schematic view illustrating a configuration example of a gas chromatograph according to an embodiment of the present invention. In the gas chromatograph, a sample is supplied together with a carrier gas into a column 1, and thus an analysis is performed. The gas chromatograph includes a column oven 2, a sample introduction unit 3, a detector 4, and the like, in addition to the column 1.

An example of the column 1 is a capillary column. The column 1 is heated in the column oven 2 during an analysis. A sample is vaporized in a sample vaporization chamber 5 formed in the sample introduction unit 3, and the vaporized sample is supplied into the column 1 together with a carrier gas. The sample supplied into the column 1 is separated while the sample passes through the column 1, and a separated sample component is detected by the detector 4. Examples of the detector 4 may include various detectors such as a flame ionization detector (FID).

In the column oven 2, a heater 21, a fan 22, and the like are provided. During an analysis, the column 1 is heated by the heater 21. After the analysis is finished, power feeding to the heater 21 is stopped as necessary, and the column 1 can be cooled by driving a motor M to rotate the fan 22. As described, since the column 1 is cooled by using the fan 22, the column 1 can be more rapidly cooled than the detector 4 and the sample vaporization chamber 5, which are naturally cooled.

A gas supply flow channel 6, a purge flow channel 7, a split flow channel 8, and the like communicate with the sample vaporization chamber 5. The gas supply flow channel 6 is a flow channel for supplying a carrier gas into the sample vaporization chamber 5. The purge flow channel 7 is a flow channel for discharging an undesired component generated from a septum or the like to the outside. The split flow channel 8 is a flow channel for discharging an excessive sample component together with the carrier gas to the outside when a carrier gas is introduced into the column 1 from the sample vaporization chamber 5 by a split injection method.

Figure 2:
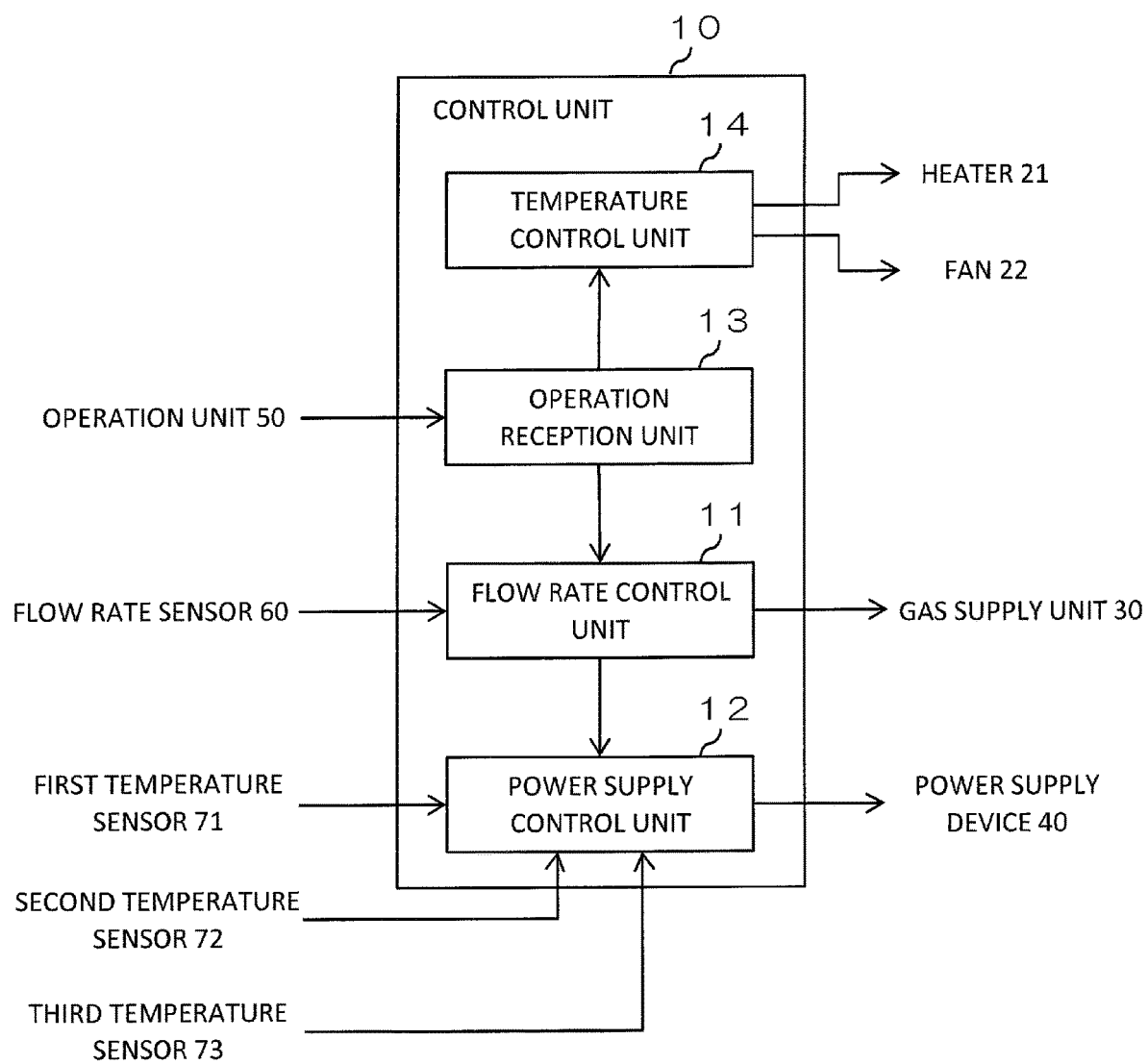
FIG. 2 is a block diagram illustrating an example of the electrical configuration in the gas chromatograph illustrated in FIG. 1.

FIG. 2 is a block diagram illustrating an example of the electrical configuration in the gas chromatograph illustrated in FIG. 1. The operation of the gas chromatograph is controlled by a control unit 10 including, for example, a CPU (Central Processing Unit). In addition to the above-described heater 21 and the above-described fan 22, a gas supply unit 30, a power supply device 40, an operation unit 50, a flow rate sensor 60, a first temperature sensor 71, a second temperature sensor 72, a third temperature sensor 73, and the like are electrically connected to the control unit 10.

The gas supply unit 30 is configured to include, for example, a gas cylinder and an AFC (electronic flow controller). The gas supply unit 30 supplies a carrier gas to the sample vaporization chamber 5 through the gas supply flow channel 6. The power supply device 40 is a device for supplying power to each unit of the gas chromatograph. The operation unit 50 is configured to include, for example, a keyboard or a mouse. An operator can perform various instruction operations for the gas chromatograph by operating the operation unit 50.

The flow rate sensor 60 detects the total flow rate of the carrier gas to be supplied to the sample vaporization chamber 5. Here, the total flow rate of the carrier gas means a sum of the flow rate of the carrier gas flowing through the column 1, the flow rate (purge flow rate) of the carrier gas flowing through the purge flow channel 7, and the flow rate (split flow rate) of the carrier gas flowing through the split flow channel 8. The first temperature sensor 71 is provided, for example, in the column oven 2, and detects the temperature of the column 1 (temperature of the column oven 2). The second temperature sensor 72 is attached, for example, to the detector 4, and detects the temperature of the detector 4. The third temperature sensor 73 is attached, for example, to the sample introduction unit 3, and detects the temperature of the sample vaporization chamber 5.

Execution of a program by the CPU causes the control unit 10 to function as a flow rate control unit 11, a power supply control unit 12, an operation reception unit 13, a temperature control unit 14, and the like. The flow rate control unit 11 controls the flow rate of the carrier gas to be supplied to the sample vaporization chamber 5. Specifically, the flow rate control unit 11 performs a process of bringing the flow rate of the carrier gas close to a target flow rate by controlling the operation of the gas supply unit 30 according to a detection signal from the flow rate sensor 60.

The power supply control unit 12 performs a process of switching over the power supply of the gas chromatograph. Specifically, the power supply control unit 12 controls the operation of the power supply device 40, and thus the power supply is switched over between an ON state where power is supplied to each unit of the gas chromatograph from the power supply device 40, and an OFF state where power is not supplied to each unit.

In a case where an instruction operation for the gas chromatograph is performed by using the operation unit 50, the operation reception unit 13 performs a process of receiving the instruction operation. In a case where a stop operation for the power supply of the gas chromatograph is performed by using the operation unit 50 and the stop operation is received by the operation reception unit 13, a process of reducing the flow rate of the carrier gas to be supplied to the sample vaporization chamber 5 is performed by the flow rate control unit 11.

In this case, the power supply control unit 12 performs a process of switching over the power supply of the gas chromatograph according to detection signals from the first temperature sensor 71, the second temperature sensor 72, and the third temperature sensor 73. Specifically, in a case where the temperature of the column 1 is not higher than a first reference temperature, the temperature of the detector 4 is not higher than a second reference temperature, and the temperature of the sample vaporization chamber 5 is not higher than a third reference temperature in a state where the flow rate of the carrier gas to be supplied to the sample vaporization chamber 5 is not greater than a reference flow rate, the power supply of the gas chromatograph is switched over from the ON state to the OFF state.

The temperature control unit 14 controls the temperature of each of the column 1, the detector 4, and the sample vaporization chamber 5. In FIG. 1, only the heater 21 for heating the column 1 is illustrated; however, during an analysis, the detector 4 and the sample vaporization chamber 5 are also heated by heaters, not illustrated. The temperature control unit 14 controls the operations of the heaters, the fan 22, and the like, and thus performs a process of bringing the temperature of each of the column 1, the detector 4, and the sample vaporization chamber 5 close to a target temperature which is manually or automatically set.

Figure 3:
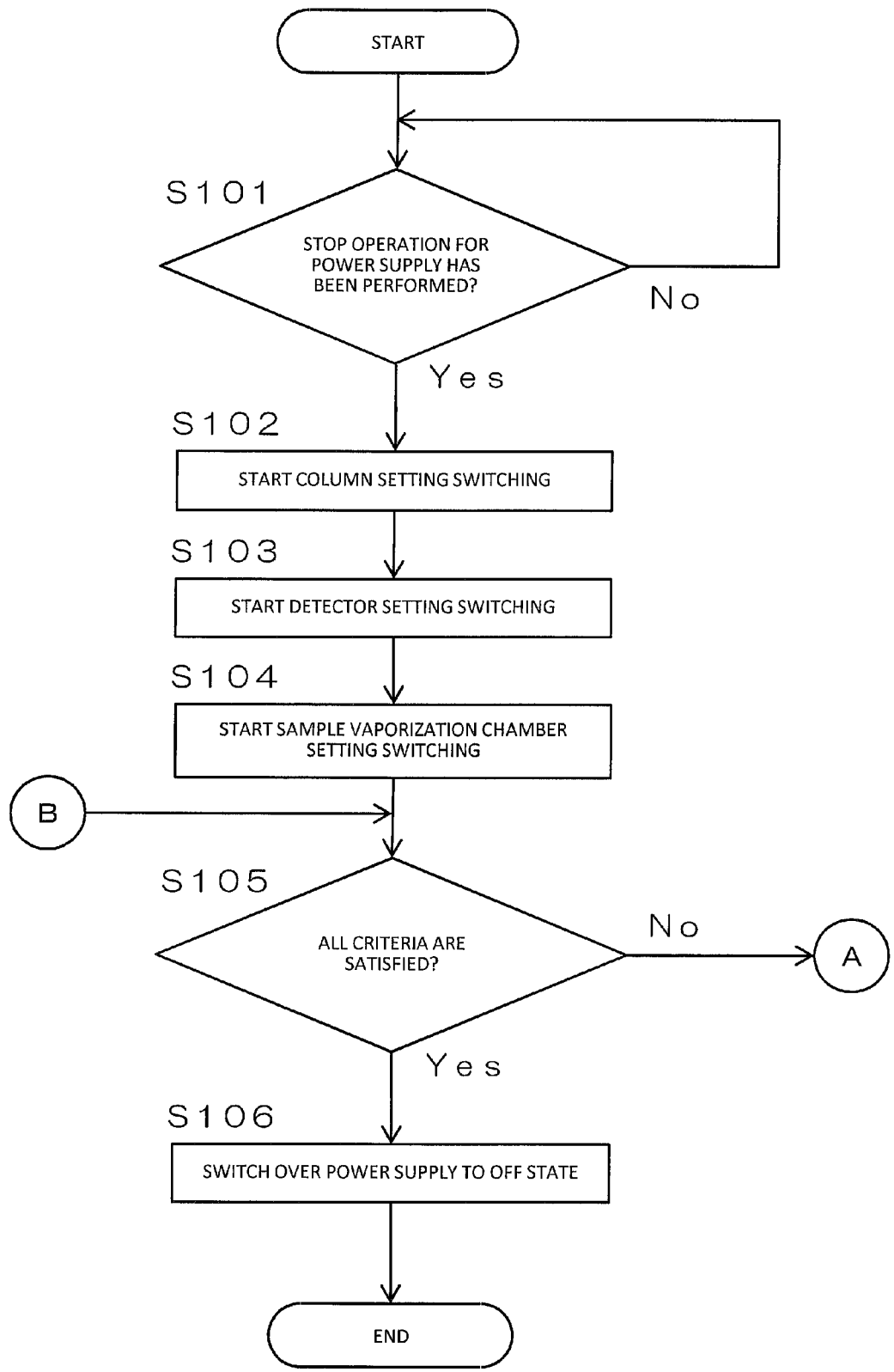
FIG. 3 is a flowchart illustrating a flow of processes performed by a control unit in a case where a stop operation for a power supply of the gas chromatograph is performed.

FIG. 3 is a flowchart illustrating a flow of processes performed by the control unit 10 in a case where a stop operation for the power supply of the gas chromatograph is performed. In a case where an operator operates the operation unit 50 and then the operation reception unit 13 receives an instruction to stop the power supply of the gas chromatograph (Yes in step S101), a process for switching over a setting regarding the column 1 (column setting switching), a process for switching over a setting regarding the detector 4 (detector setting switching), and a process for switching over settings regarding the sample vaporization chamber 5 (sample vaporization chamber setting switching) are initiated (steps S102 to S104).

Thereafter, it is judged whether or not all the specific criteria are satisfied in the column 1, the detector 4, and the sample vaporization chamber 5 (step S105). This judgment is for judging whether or not to switch over the power supply of the gas chromatograph from the ON state to the OFF state. Temperatures of the column 1, the detector 4, and the sample vaporization chamber 5 (first to third reference temperatures), a flow rate of a carrier gas (reference flow rate), and the like are used as criteria for judgement.

In a case where all the specific criteria are satisfied in the column 1, the detector 4, and the sample vaporization chamber 5 (Yes in step S105), the power supply control unit 12 controls the operation of the power supply device 40, and thus the power supply of the gas chromatograph is automatically switched over from the ON state to the OFF state (step S106). In contrast, during a period in which at least one of the criteria is not satisfied (No in step S105), corresponding processes from among the processes illustrated in FIGS. 4 to 6, to be described later, are repeated. Note that the OFF state of the power supply of the gas chromatograph includes not only a state where no power is supplied to the gas chromatograph but also a state where a very small amount of power is supplied to the gas chromatograph.

Figure 4:
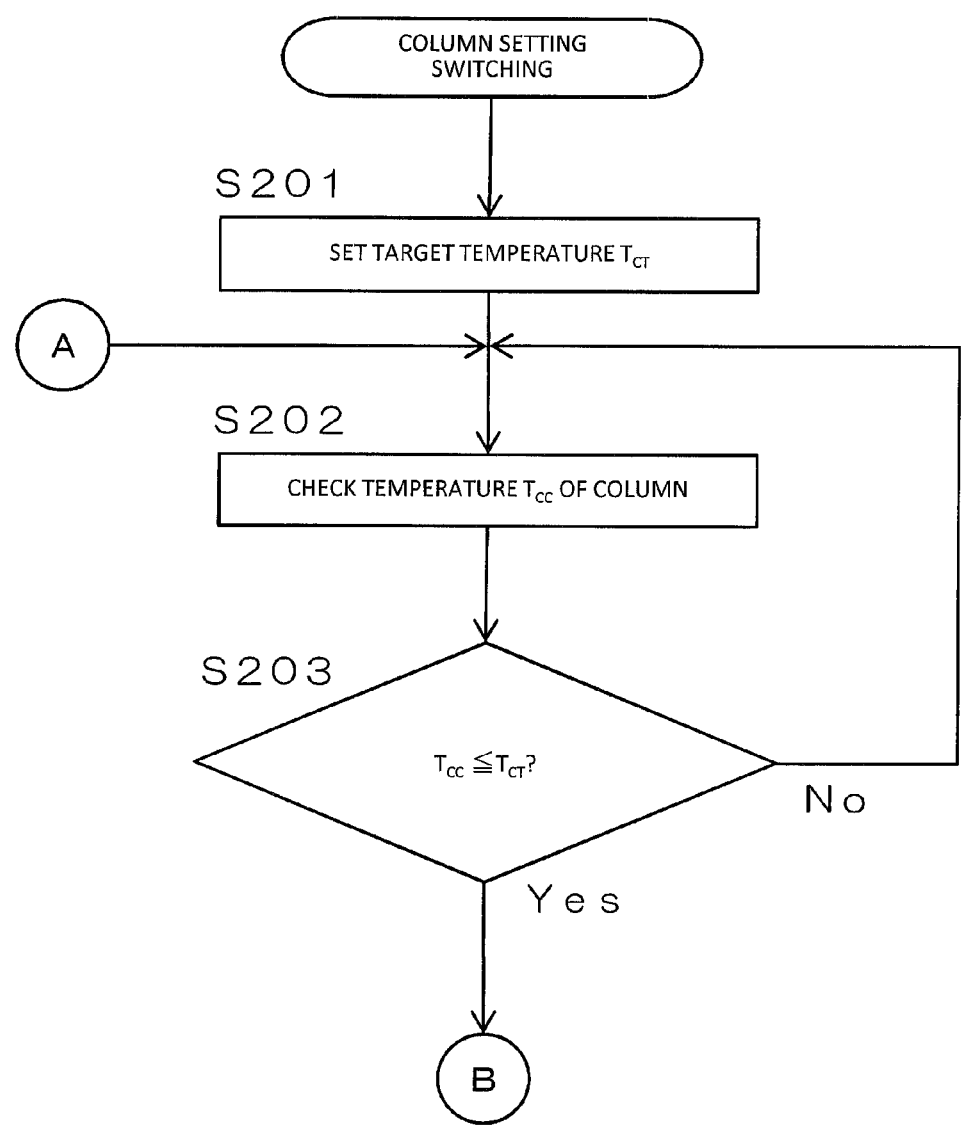
FIG. 4 is a flowchart illustrating a manner of column setting switching.

FIG. 4 is a flowchart illustrating a manner of column setting switching. In a case where an instruction to stop the power supply of the gas chromatograph is given, a target temperature $T_CT$ of the column 1 is set by the temperature control unit 14 (step S201). The target temperature $T_{CT}$ of the column 1 is equal to the temperature of the column 1 (first reference temperature) which is one of the criteria for judgment as to whether or not to switch over the power supply of the gas chromatograph from the ON state to the OFF state, or is lower than the first reference temperature.

Thereafter, a temperature $T_{CC}$ of the column 1 is continuously checked according to a detection signal from the first temperature sensor 71 (step S202), until the temperature $T_{CC}$ of the column 1 becomes not higher than the target temperature $T_{CT}$ (until Yes is obtained in step S203). Then, in a case where the temperature $T_{CC}$ of the column 1 is not higher than the target temperature $T_{CT}$, that is, not higher than the first reference temperature (Yes in step S203), judgement in step S105 in FIG. 3 is made. In a case where not all the criteria are satisfied in judgment in step S105 (No in step S105), the processes in steps S202 and S203 are performed again.

Figure 5:
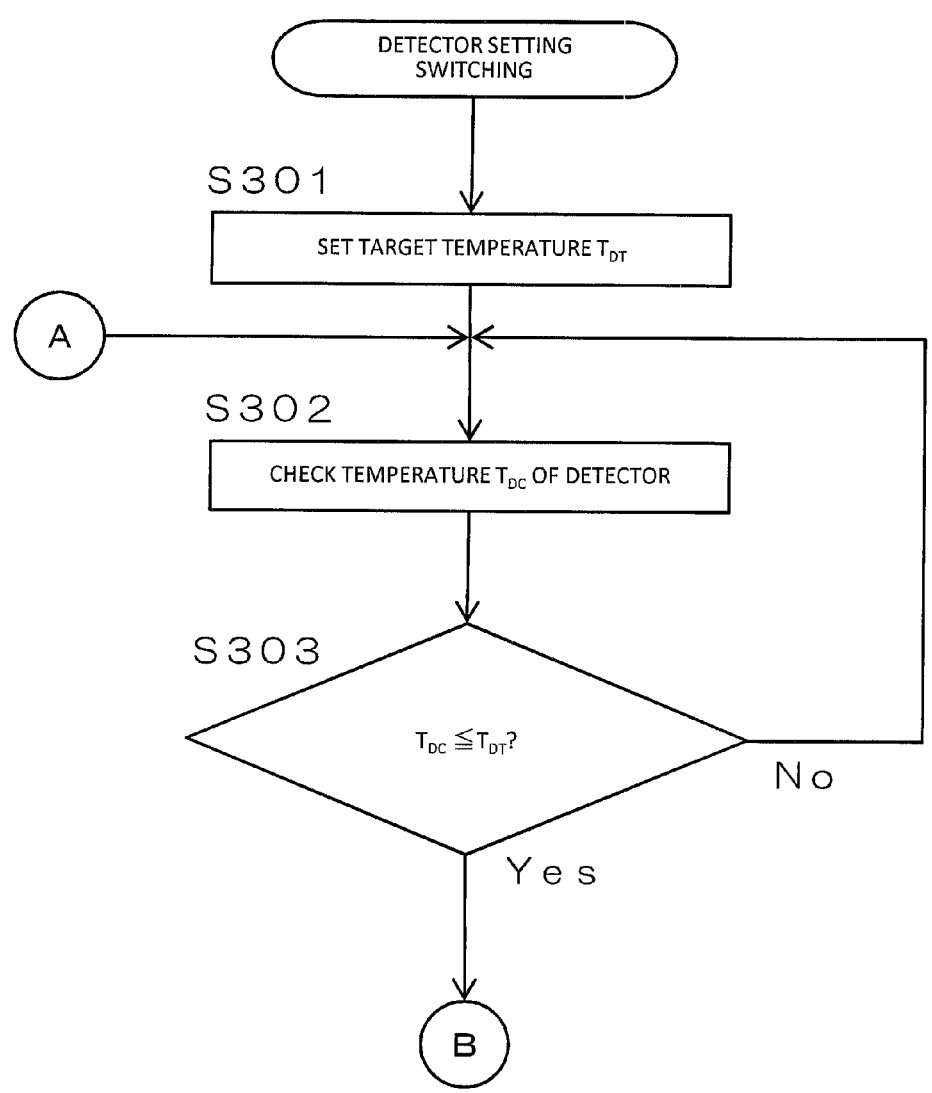
FIG. 5 is a flowchart illustrating a manner of detector setting switching.

FIG. 5 is a flowchart illustrating a manner of detector setting switching. In a case where an instruction to stop the power supply of the gas chromatograph is given, a target temperature $T_{DT}$ of the detector 4 is set by the temperature control unit 14 (step S301). The target temperature $T_{DT}$ of the detector 4 is equal to the temperature of the detector 4 (second reference temperature) which is one of the criteria for judgment as to whether or not to switch over the power supply of the gas chromatograph from the ON state to the OFF state, or is lower than the second reference temperature.

Thereafter, a temperature $T_{DC}$ of the detector 4 is continuously checked according to a detection signal from the second temperature sensor 72 (step S302), until the temperature $T_{DC}$ of the detector 4 becomes not higher than the target temperature $T_{DT}$ (until Yes is obtained in step S303). Then, in a case where the temperature $T_{DC}$ of the detector 4 is not higher than the target temperature $T_{DT}$, that is, not higher than the second reference temperature (Yes in step S303), judgement in step S105 in FIG. 3 is made. In a case where not all the criteria are satisfied in judgment in step S105 (No in step S105), the processes in steps S302 and S303 are performed again.

Figure 6:
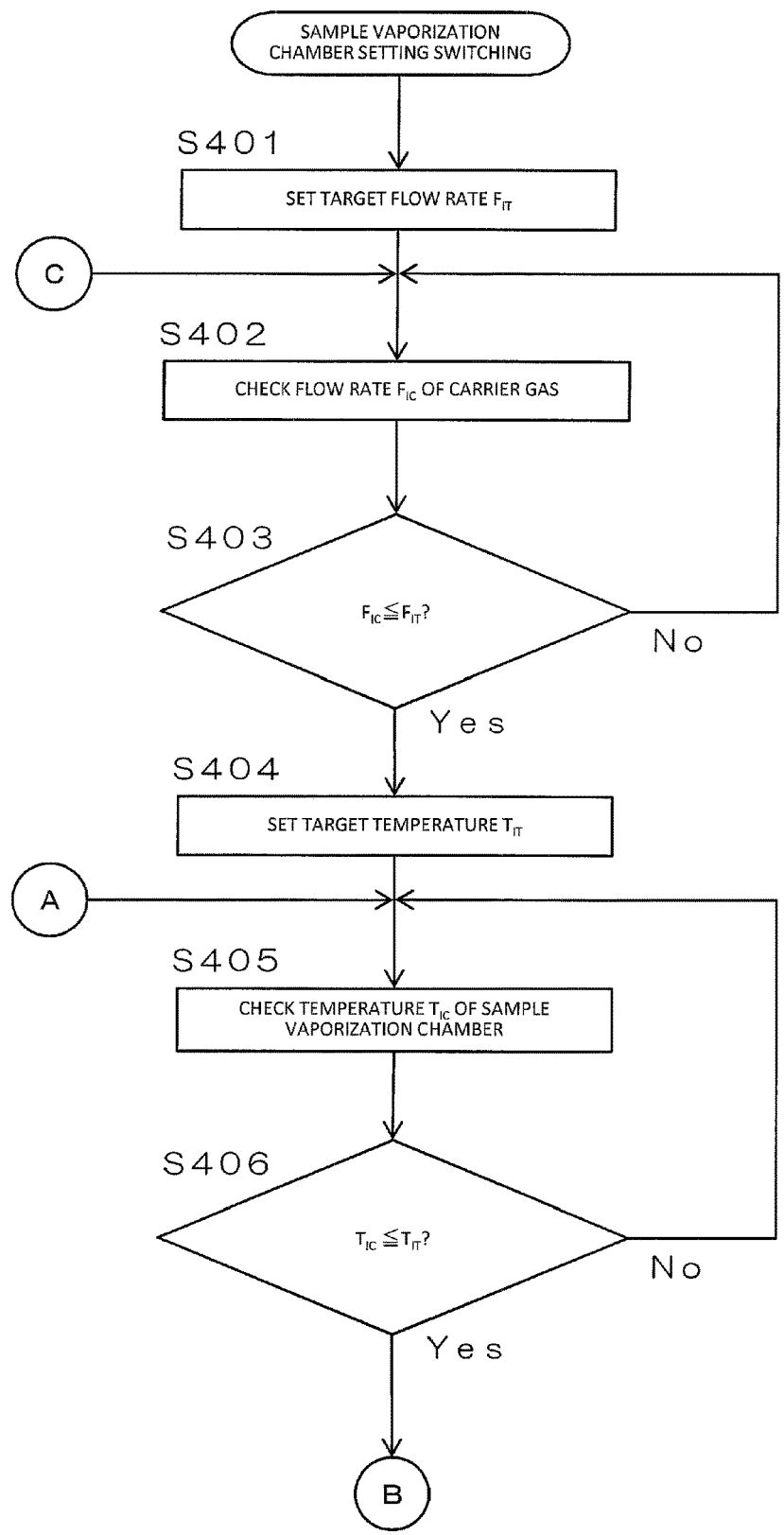
FIG. 6 is a flowchart illustrating a manner of sample vaporization chamber setting switching.

FIG. 6 is a flowchart illustrating a manner of sample vaporization chamber setting switching. In a case where an instruction to stop the power supply of the gas chromatograph is given, a target flow rate $F_{IT}$ of the carrier gas is set by the flow rate control unit 11 (step S401), and the flow rate of the carrier gas is controlled such that the flow rate is close to the target flow rate $F_{IT}$. The target flow rate $F_{IT}$ of the carrier gas is less than the flow rate of the carrier gas upon analysis, and is set to a flow rate which does not cause damages to the column 1 and the detector 4 due to high temperature.

Thereafter, a flow rate $F_{IC}$ of the carrier gas is continuously checked according to a detection signal from the flow rate sensor 60 (step S402), until the flow rate $F_{IC}$ of the carrier gas becomes not greater than the target flow rate $F_{IT}$ (until Yes is obtained in step S403). In the present embodiment, a description will be given of a case where a flow rate of the carrier gas which is one of the criteria for judgement as to whether or not to switch over the power supply of the gas chromatograph from the ON state to the OFF state (reference flow rate), is equal to the target flow rate $F_{IT}$; however, the target flow rate $F_{IT}$ may be any fixed flow rate not greater than the reference flow rate.

In a case where the flow rate $F_{IC}$ of the carrier gas is not greater than the target flow rate $F_{IT}$, that is, not greater than the reference flow rate (Yes in step S403), a target temperature $T_{IT}$ of the sample vaporization chamber 5 is set by the temperature control unit 14 (step S404). The target temperature $T_{IT}$ of the sample vaporization chamber 5 is equal to the temperature of the sample vaporization chamber 5 (third reference temperature) which is one of the criteria for judgment as to whether or not to switch over the power supply of the gas chromatograph from the ON state to the OFF state, or is lower than the third reference temperature.

Thereafter, a temperature $T_{IC}$ of the sample vaporization chamber 5 is continuously checked according to a detection signal from the third temperature sensor 73 (step S405), until the temperature $T_{IC}$ of the sample vaporization chamber 5 becomes not higher than the target temperature $T_{IT}$ (until Yes is obtained in step S406). Then, in a case where the temperature $T_{IC}$ of the sample vaporization chamber 5 is not higher than the target temperature $T_{IT}$, that is, not higher than the third reference temperature (Yes in step S406), judgement in step S105 in FIG. 3 is made. In a case where not all the criteria are satisfied in the judgment in step S105 (No in step S105), the processes in steps S405 and S406 are performed again.

As described above, in the present embodiment, in a case where a stop operation for the power supply of the gas chromatograph is performed (Yes in step S101), the power supply of the gas chromatograph can be switched over from the ON state to the OFF state (step S106) after the flow rate of the carrier gas to be supplied to the sample vaporization chamber 5 has been decreased (steps S401 to S403), and the temperatures of the column 1, the detector 4, and the sample vaporization chamber 5 have been sufficiently lowered (steps S201 to S203, S301 to S303, and S404 to S406). As described, by reducing the flow rate of the carrier gas at a time point when a stop operation for the power supply of the gas chromatograph is performed, the amount consumed of the carrier gas can be effectively reduced.

Even in a case where the flow rate of the carrier gas is reduced, since the carrier gas constantly flows into the column 1 and the detector 4 even though the amount of the carrier gas may be small, the column 1 and the detector 4 can be constantly filled with the carrier gas at room temperature, and damages to the column 1 and the detector 4 due to high temperature can be prevented. In addition, since the power supply of the gas chromatograph is switched over from the ON state to the OFF state after the temperatures of the column 1 and the detector 4 have been sufficiently lowered, damages to the column 1 and the detector 4 can be prevented even after the power supply has been switched over to the OFF state. By automatically performing such control, the time and effort required for an operator to manually set parameters can be reduced and damages to the column 1 and the detector 4 due to a setting mistake can be prevented.

Figure 7:
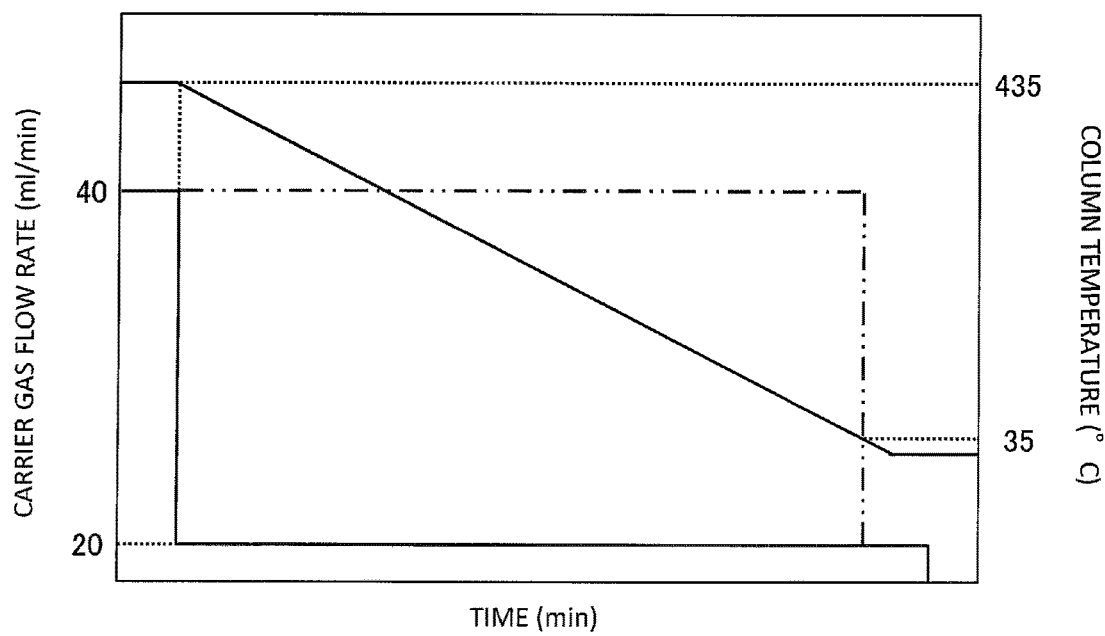
FIG. 7 is a diagram illustrating an example of changes in the temperature of a column and the flow rate of a carrier gas.

FIG. 7 is a diagram illustrating an example of changes in the temperature of the column 1 and the flow rate of the carrier gas. This example illustrates a case where a stop operation for the power supply of the gas chromatograph is performed when the temperature of the column 1 is 435° C. In this case, at a time point when the stop operation for the power supply of the gas chromatograph is performed, the flow rate of the carrier gas is decreased from 40 ml/min to 20 ml/min, which is not greater than the reference flow rate.

In addition, at the time point when the stop operation for the power supply of the gas chromatograph is performed, the target temperature of the column 1 is set to 35° C. (second reference temperature) or is set to be lower than that, and thus the temperature of the column 1 is gradually lowered. Then, when all the other criteria (temperatures of the column 1 and the sample vaporization chamber 5, and the like) are satisfied after the temperature of the column 1 becomes not higher than 35° C., the power supply of the gas chromatograph is switched over from the ON state to the OFF state, and supply of the carrier gas is stopped.

In a case of a conventional configuration where the flow rate of the carrier gas is decreased at a time point when the temperature of the column 1 becomes not higher than 35° C., the amount consumed of the carrier gas is large as indicated by an alternate long and two short dashed line in FIG. 7. In contrast, if the flow rate of the carrier gas is rapidly decreased to be not higher than the reference flow rate at a time point when the stop operation for the power supply of the gas chromatograph is performed, the amount consumed of the carrier gas can be effectively reduced.

Figure 8:
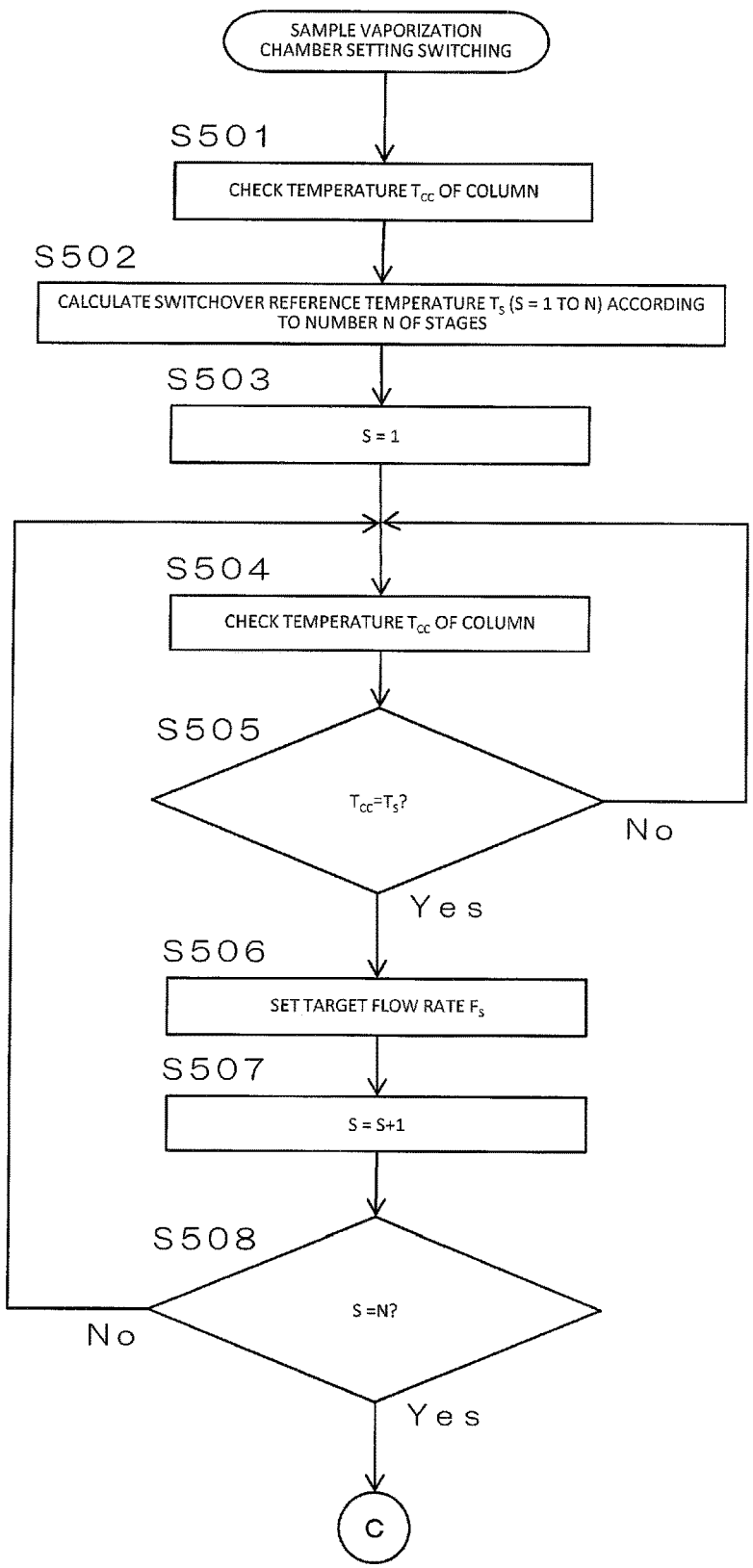
FIG. 8 is a flowchart illustrating a modification of the sample vaporization chamber setting switching.
Figure 9:
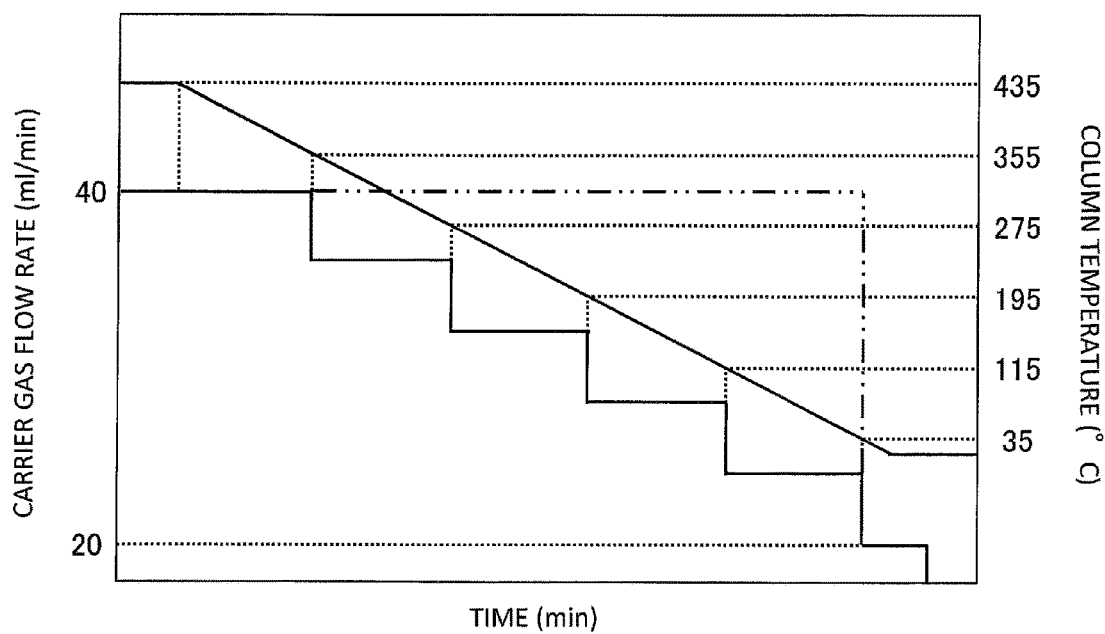
FIG. 9 is a diagram illustrating an example of changes in the temperature of a column and the flow rate of a carrier gas in the modification illustrated in FIG. 8.

FIG. 8 is a flowchart illustrating a modification of the sample vaporization chamber setting switching. In addition, FIG. 9 is a diagram illustrating an example of changes in the temperature of the column 1 and the flow rate of a carrier gas in the modification illustrated in FIG. 8. In this example, in a case where a stop operation for the power supply of the gas chromatograph is performed, the target flow rate of the carrier gas is decreased in stages to a flow rate not greater than the reference flow rate instead of rapidly decreasing the target flow rate to a fixed flow rate not greater than the reference flow rate. For example, an operator may operate the operation unit 50 to set in advance the number N of stages to any value, the number N being used when the flow rate of the carrier gas is decreased in stages.

In a case where an instruction to stop the power supply of the gas chromatograph is received by the operation reception unit 13, the temperature $T_{CC}$ of the column 1 is checked according to a detection signal from the second temperature sensor 72 (step S501). Then, according to the temperature $T_{CC}$ of the column 1, the target flow rate of the carrier gas to be supplied to the sample vaporization chamber 5 is decreased in stages to a flow rate not greater than the reference flow rate. Specifically, a switchover reference temperature $T_S$ (S=1 to N) of the column 1 upon switchover of the flow rate of the carrier gas in each stage is calculated according to the temperature $T_{CC}$ of the column 1 and the number N of stages (step S502).

The example in FIG. 9 illustrates a case where the temperature $T_{CC}$ of the column 1 is 435° C., the second reference temperature is 35° C., and the number N of stages is "5". The value obtained by dividing the difference (435−35=400° C.) between the temperature $T_{CC}$ of the column 1 and the second reference temperature by the number N of stages (400/5=80° C.) is calculated as the difference between switchover reference temperatures $T_S$ (S=1 to 5). Therefore, in the example illustrated in FIG. 9, the switchover reference temperatures $T_S$ (S=1 to 5) are calculated as follows.

$T_1 = 435 - 80 = 355°$ C.

$T_2 = 355 - 80 = 275°$ C.

$T_3 = 275 - 80 = 195°$ C.

$T_4 = 195 - 80 = 115°$ C.

$T_5 = 115 - 80 = 35°$ C.

Thereafter, S=1 is set (step S503). The temperature $T_{CC}$ of the column 1 is continuously checked according to a detection signal from the second temperature sensor 72 (step S504) until the temperature $T_{CC}$ of the column 1 becomes the switchover reference temperature $T_1$ (until Yes is obtained in step S505). Then, a target flow rate $F_1$ of the carrier gas is set at a time point when the temperature $T_{CC}$ of the column 1 becomes the switchover reference temperature $T_1$ (Yes in step S505), and thus the flow rate $F_{IC}$ of the corrier gas is decreased.

Thereafter, S is sequentially incremented (step 507), and thus the processes in steps S504 to S508 are repeated until S=N is satisfied (until Yes is obtained in step S508). Therefore, every time the temperature $T_{CC}$ of the column 1 becomes the switchover reference temperature $T_S$ (S=1 to N), the target flow rate $F_S$ (S=1 to N) of the carrier gas is set, and the flow rate $F_{IC}$ of the carrier gas is decreased in stages. Note that the relationship between the temperature $T_{CC}$ of the column 1 and the target flow rate $F_S$ (S=1 to N) of the carrier gas is set in advance, and the target flow rate $F_S$ is set according to the relationship.

After S=N has been satisfied (Yes in step S508), the processes similar to those in step S402 and the subsequent steps in FIG. 6 are performed. That is, the flow rate $F_{IC}$ of the carrier gas is continuously checked according to a detection signal from the flow rate sensor 60 (step S402) until the flow rate $F_{IC}$ of the carrier gas becomes not greater than the target flow rate $F_{IT}$ (=$F_S$) (until Yes is obtained in step S403). In a case where the flow rate $F_{IC}$ of the carrier gas is not greater than the target flow rate $F_{IT}$ (Yes in step S403), the target temperature $T_{IT}$ of the sample vaporization chamber 5 is set by the temperature control unit 14 (step S404).

Thereafter, until the temperature $T_{IC}$ of the sample vaporization chamber 5 becomes not higher than the target temperature $T_{IT}$ (until Yes is obtained in step S406), the temperature $T_{IC}$ of the sample vaporization chamber 5 is continuously checked according to a detection signal from the third temperature sensor 73 (step S405). Then, in a case where the temperature $T_{IC}$ of the sample vaporization chamber 5 is not higher than the target temperature $T_{IT}$, that is, not higher than the third reference temperature (Yes in step S406), judgment in step S105 in FIG. 3 is made. In the judgment in step S105, in a case where not all the criteria are satisfied (No in step S105), the processes in steps S405 and S406 are performed again.

As described, in the above modification, in a case where a stop operation for the power supply of the gas chromatograph is performed, since the flow rate of the carrier gas is decreased in stages to be not greater than the reference flow rate, the flow rate of the carrier gas can be gradually decreased while the temperatures of the column 1 and the detector 4 are lowered. At that time, since the flow rate of the carrier gas is gradually reduced according to the temperature of the column 1, the amount consumed of the carrier gas can be more effectively reduced than in a conventional case indicated by an alternate long and two short dashed line in FIG. 9 while a damage to the column 1 is prevented.

Figure 10:
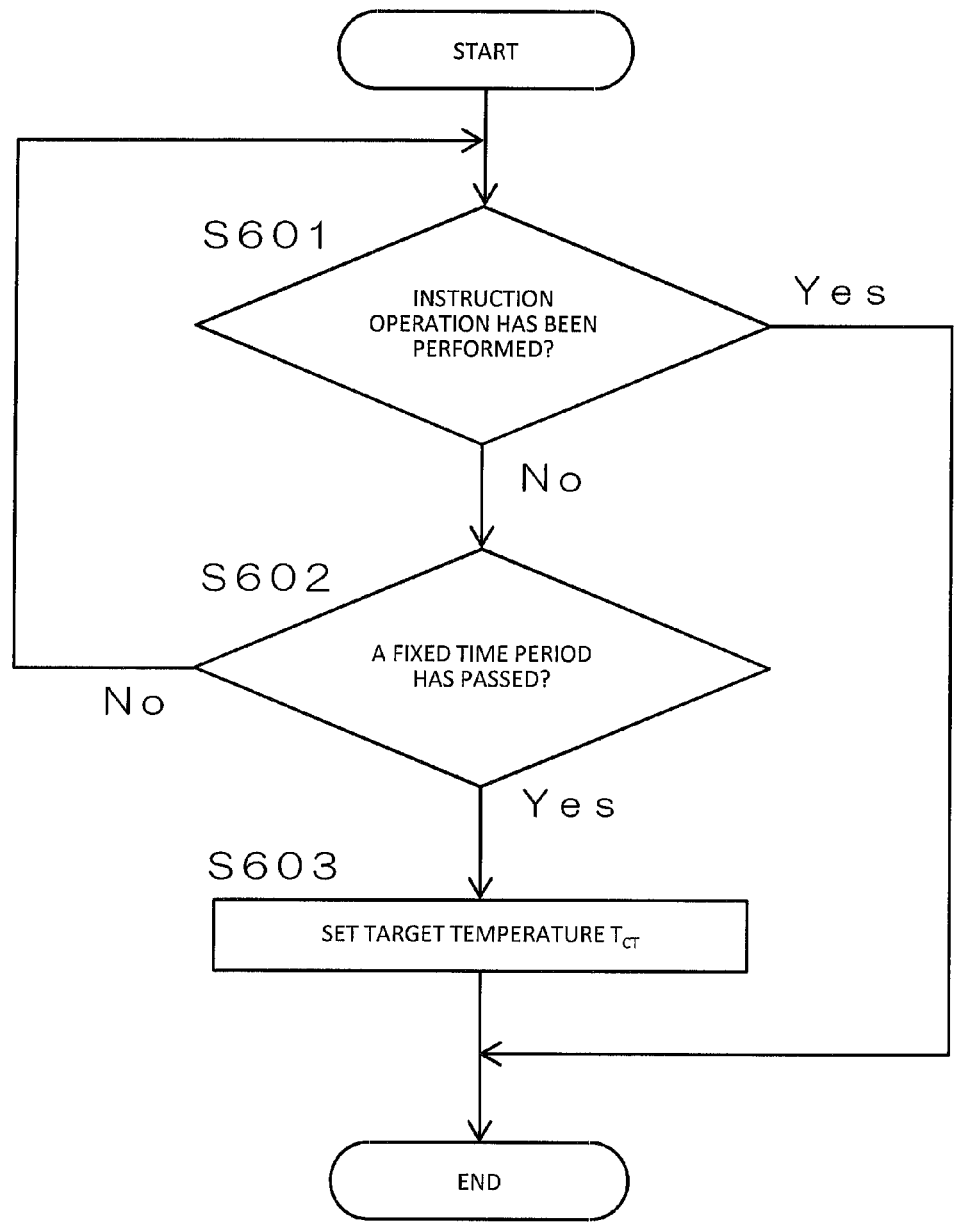
FIG. 10 is a flowchart illustrating a flow of processes performed by the control unit in a case where no instruction operation for the gas chromatograph is performed.

FIG. 10 is a flowchart illustrating a flow of processes performed by the control unit 10 in a case where no instruction operation for the gas chromatograph is performed. When the power supply of the gas chromatograph is in the ON state, it is monitored whether or not a fixed time period has passed without an operation for the operation unit 50 by an operator.

Then, in a case where a fixed time period has passed (Yes in step S602) in a state where no operation for the operation unit 50 is performed by an operator and no instruction operation for the gas chromatograph is received by the operation reception unit 13 (No in step S601), the target temperature $T_{CT}$ of the column 1 is automatically set by the temperature control unit 14 (step S603) in a state where supply of the carrier gas into the column 1 is maintained. The target temperature $T_{CT}$ of the column 1 set at that time is a temperature lower than the temperature of the column 1 during an analysis, and is a temperature (for example, room temperature) which does not cause a damage to the column 1 such as bleed even if the column 1 is maintained at the temperature for a long time.

As described, in the present embodiment, in a case where an operator does not perform an instruction operation for the gas chromatograph for a long time, the temperature of the column 1 is automatically lowered. Therefore, a damage to the column 1 can be effectively prevented. Note that the processes as illustrated in FIG. 10 can also be applied to a gas chromatograph which does not perform the processes as illustrated in FIGS. 3 to 6, and 8.

In the above embodiment, the configuration has been described where the power supply of the gas chromatograph is switched over from the ON state to the OFF state in a case where the temperature of the column 1 is not higher than the first reference temperature, the temperature of the detector 4 is not higher than the second reference temperature, and the temperature of the sample vaporization chamber 5 is not higher than the third reference temperature in a state where the flow rate of the carrier gas to be supplied to the sample vaporization chamber 5 is not greater than the reference flow rate. However, the present invention is not limited to this, and a configuration may be adopted where the temperature of the sample vaporization chamber 5 is not used as a criterion. In this case, the power supply of the gas chromatograph may be switched over from the ON state to the OFF state in a case where the temperature of the column 1 is not higher than the first reference temperature and the temperature of the detector 4 is not higher than the second reference temperature in a state where the flow rate of the carrier gas to be supplied to the sample vaporization chamber 5 is not greater than the reference flow rate.

DESCRIPTION OF REFERENCE SIGNS 1 column
2 column oven
3 sample introduction unit
4 detector
5 sample vaporization chamber
6 gas supply flow channel
7 purge flow channel
8 split flow channel
10 control unit
11 flow rate control unit
12 power supply control unit
13 operation reception unit
14 temperature control unit
21 heater
22 fan
30 gas supply unit
40 power supply device
50 operation unit
60 flow rate sensor
71 first temperature sensor
72 second temperature sensor
73 third temperature sensor

The invention claimed is:

1. A gas chromatograph which introduces a sample, which is vaporized in a sample vaporization chamber, into a column, together with a carrier gas, and which detects a sample component which is separated while the sample passes through the column by means of a detector, the gas chromatograph comprising:
a first temperature sensor which detects a temperature of the column;
a second temperature sensor which detects a temperature of the detector;
a flow rate control unit which controls a flow rate of the carrier gas to be supplied to the sample vaporization chamber;
an operation reception unit which receives an instruction operation for the gas chromatograph; and
a power supply control unit which switches over a power supply of the gas chromatograph,
wherein
the flow rate control unit decreases a flow rate of the carrier gas to be supplied to the sample vaporization chamber in a case where a stop operation for the power supply of the gas chromatograph is received by the operation reception unit,
the power supply control unit switches over the power supply of the gas chromatograph from an ON state to an OFF state in accordance with a judgment that all of the following conditions are met:
a temperature of the column which is detected by the first temperature sensor is not higher than a first reference temperature,
a temperature of the detector which is detected by the second temperature sensor is not higher than a second reference temperature, and
a flow rate of the carrier gas to be supplied to the sample vaporization chamber has been decreased by the flow rate control unit, and the flow rate of the carrier gas to be supplied to the sample vaporization chamber is not greater than a reference flow rate,
wherein the reference flow rate is less than the flow rate of the carrier gas upon analysis, greater than no flow rate, and is a flow rate which does not cause damages to the column and the detector.

2. The gas chromatograph according to claim 1, wherein
in a case where a stop operation for the power supply of the gas chromatograph is received by the operation reception unit, the flow rate control unit sets a target flow rate of a carrier gas to be supplied to the sample vaporization chamber to a fixed flow rate which is not greater than the reference flow rate.

3. The gas chromatograph according to claim 1, wherein
the flow rate control unit decreases in stages a target flow rate of a carrier gas to be supplied to the sample vaporization chamber to a flow rate which is not greater than the reference flow rate according to a temperature of the column which is detected by the first temperature sensor in a case where a stop operation for the power supply of the gas chromatograph is received by the operation reception unit.

4. The gas chromatograph according to claim 1 further comprising:
a temperature control unit which automatically lowers a target temperature of the column in a case where a fixed time period has passed in a state where no instruction operation for the gas chromatograph is received by the operation reception unit when the power supply of the gas chromatograph is in an ON state.

5. The gas chromatograph according to claim 1, wherein the flow rate control unit decreases the flow rate of the carrier gas so as to supply a relatively smaller flow of carrier gas to be supplied to the sample vaporization chamber in the case where the stop operation for the power supply of the gas chromatograph is received by the operation reception unit.

6. The gas chromatograph according to claim 1 further comprising:
   a third temperature sensor which detects a temperature of the sample vaporization chamber,
   wherein
   the power supply control unit switches over the power supply of the gas chromatograph from an ON state to an OFF state in a case where a temperature of the column which detected by the first temperature sensor is not higher than the first reference temperature, a temperature of the detector which is detected by the second temperature sensor is not higher than the second reference temperature, and a temperature of the sample vaporization chamber which is detected by the third temperature sensor is not higher than a third reference temperature in a state where a flow rate of a carrier gas to be supplied to the sample vaporization chamber is not greater than the reference flow rate.

7. A gas chromatography method for a gas chromatograph configured to introduce a sample, which is vaporized in a sample vaporization chamber, into a column, together with a carrier gas, and detect a sample component which is separated while the sample passes through the column by means of a detector, the method comprising:
   an operation reception step of receiving an instruction operation for the gas chromatograph,
   a flow rate control step of controlling a flow rate of the carrier gas supplied to the sample vaporization chamber, the flow rate control step including decreasing a flow rate of the carrier gas supplied to the sample vaporization chamber in response to the instruction operation being for stopping a power supply of the gas chromatograph, and
   a power supply control step of switching over the power supply of the gas chromatograph, such that the power supply control step switches over the power supply of the gas chromatograph from an ON state to an OFF state in accordance with a judgment that all of the following conditions are met:
      a temperature of the column which is detected by a first temperature sensor is not higher than a first reference temperature,
      a temperature of the detector which is detected by a second temperature sensor is not higher than a second reference temperature, and
      the flow rate of the carrier gas to be supplied to the sample vaporization chamber has been decreased in the flow rate control step, and, after the decrease, the flow rate of the carrier gas to be supplied to the sample vaporization chamber is not greater than a reference flow rate,
   wherein the reference flow rate is less than the flow rate of the carrier gas upon analysis, greater than no flow rate, and is a flow rate which does not cause damages to the column and the detector.

* * * * *